US006454944B1

(12) United States Patent
Raven (10) Patent No.: US 6,454,944 B1
(45) Date of Patent: Sep. 24, 2002

(54) PROCESS AND APPARATUS FOR CONVERSION OF BIODEGRADABLE ORGANIC MATERIALS INTO PRODUCT GAS

(76) Inventor: Larry J. Raven, 3504 E. Huntington Blvd., Fresno, CA (US) 93703

( * ) Notice: Subject to any disclaimer, the term of this patent is extended or adjusted under 35 U.S.C. 154(b) by 0 days.

(21) Appl. No.: 10/121,256

(22) Filed: Apr. 12, 2002

Related U.S. Application Data (63) Continuation-in-part of application No. 09/709,025, filed on Nov. 8, 2000, now abandoned.

(51) Int. Cl.$^7$ .................................................. C02F 3/00
(52) U.S. Cl. ...................................... 210/603; 210/180
(58) Field of Search .............................. 210/603, 605, 210/609, 612, 613, 180

(56) References Cited

U.S. PATENT DOCUMENTS

| | | |
|---|---|---|
| 1,806,698 A | 5/1931 | Miller |
| 1,838,474 A | 12/1931 | Buswell et al. |
| 1,838,475 A | 12/1931 | Buswell |
| 1,880,773 A | 10/1932 | Buswell et al. |
| 4,022,665 A | 5/1977 | Ghosh et al. |
| 4,040,953 A | 8/1977 | Ort |
| 4,157,958 A | 6/1979 | Chow |
| 4,208,279 A | 6/1980 | Varani |
| 4,272,374 A | 6/1981 | Baker |
| 4,274,838 A | 6/1981 | Dale et al. |
| 4,289,625 A | 9/1981 | Tarman et al. |
| 4,311,593 A | 1/1982 | Benjes et al. |
| 4,316,961 A | 2/1982 | Klass et al. |
| 4,329,428 A | 5/1982 | Ghosh et al. |
| 4,351,729 A | 9/1982 | Witt |
| 4,372,856 A | 2/1983 | Morrison |
| 4,388,186 A | 6/1983 | Fujimoto et al. |
| 4,396,402 A | 8/1983 | Ghosh |
| 4,424,064 A | 1/1984 | Klass et al. |
| 4,505,819 A | 3/1985 | Barnes et al. |
| 4,735,724 A | 4/1988 | Chynoweth et al. |
| 5,723,048 A | 3/1998 | Kobayashi et al. |
| 5,746,919 A | 5/1998 | Dague et al. |
| 6,113,798 A | 9/2000 | Burke |

FOREIGN PATENT DOCUMENTS

| | | |
|---|---|---|
| CH | 649576 | 5/1985 |
| DE | 207696 | 3/1909 |
| DE | 0044948 | 2/1982 |
| JP | 128198 | 7/1983 |

OTHER PUBLICATIONS

G. Lettinga et al, Anaerobic Treatment of Raw Domestic Sewage at Ambient Temperature Using a GranularBed UASB Reactor, Biotechnology and Bioengineering, vol. XXV p. 1701–1723 (1983).

Graham F. Andrews, "Fluidized–Bed Fermenters: A Steady–State Analysis" Biotechnology and Bioengineering, vol. XXIV pp. 2013–2030 (1982).

Donald L. Klass, et al "Methane Production by Anaerobic Digestion of Bermuda Glass", presented at Symposium on Biomass as Nonfossil Fuel Source ACS/Chemical Society of Japan Joint Chemical Congress, Honululu, HI Apr. 1–6, 1979.

(List continued on next page.)

Primary Examiner—Chester T. Barry
(74) Attorney, Agent, or Firm—Mark D. Miller (57) ABSTRACT

A method and apparatus for efficiently generating biogas from feedstocks composed of 10 to 100 percent biodegradable solids including carbohydrates, starches and/or sugars, for a variety of uses including the creation of electricity. The apparatus includes a thermophilic digester and a mesophilic digester used in series, in communication with a feedstock supply system. The digesters may be established as a stand-alone system or made part of a wastewater treatment facility. By carefully metering the specialized feedstocks into and between the digesters, maximum production of biogas can be achieved. The biogas may then be burned as part of an electricity generating process, or stored for later use.

34 Claims, 5 Drawing Sheets

OTHER PUBLICATIONS

Richard P. Lecuyer, "An Economic Assessment of Fuelgas from Water Hyacinths" and Jerome H. Marten Symposium Papers, Clean Fuels from Biomass, Sewage, Urban Refuse, Agricultural Wastes, Orlando, Florida, Jan. 27–30, 1976.

Kefa V O Rabah, "Application of Sugarcane Residues as Biofuel for Cogeneration of Electricity in Kenya", Turkey Jan. 2000 Article 13 pgs.

Water Environment Federation "Operation of Municipal Wastewater Treatment Plans" fifth edition, manual of practice, vol. 3, 24 pgs total.

Agricultural Statistics 2000, for corn, oats, molasses, sugar 19 pgs.

Webster's Dictionary, definitions for carbohydrate, corn syrup, flour, molasses, starch, sugar, 6 pgs.

Perry McCarty, One Hundred Years of Anaerobic Treatment: Dept. of Civil Engineering, Terman Engineering Center presented at Second International Conf. in Germany 9-7-81.

G. Lettinga, A. Th. Van Der Geest, S. Hobma and J.V.D. Laan "Anaerobic Treatment of Methanolic Wastes" Water Research vol. 13, pp. 725 to 737, Pergamon Press Ltd. (1979).

G. Lettinga et al, "Upflow Sludge Blanket Processes", 3rd International Symposium on Anaerobic Digestion 1983, Cambridge MA.-

PROCESS AND APPARATUS FOR CONVERSION OF BIODEGRADABLE ORGANIC MATERIALS INTO PRODUCT GAS

This application is a continuation-in-part of application Ser. No. 09/709,025 filed on Nov. 08, 2000, now abandoned.

BACKGROUND OF THE INVENTION

1. Field of the Invention

This invention relates to the production of methane and other combustible gasses useful for generating power by converting non-toxic biodegradable organic materials and high solids such as sugar, starch and/or carbohydrates into a product gas. The gas is composed primarily of methane, carbon dioxide and hydrogen. Power may be produced by further burning the gas in a boiler or other suitable engine or generator to create electricity. The electricity may be used for operation of the gas-production plant itself, and any excess electricity made available for sale to others where it may be used in engines, cars, trucks, busses, etc. The gas may also be used as fuel for gas fired engine generators for peaker plants. Alternatively, the gas may be scrubbed and sold as clean gas to offset the use of natural gas.

2. Description of the Prior Art

The production of methane and other usable biogases by anaerobic digestion of various organic wastes, particularly sewage sludge organic waste, is well known. The organic feed mixture which provides the substrate for anaerobic biodegradation may comprise a wide variety of organic carbon sources. Many digester designs, feed stocks, mixtures and additives have been proposed to increase the methane yield and to provide greater conversion efficiency of organic materials to useful products.

The production of biogas was discovered in the seventeenth century. Today, biogases such as methane are commonly produced at municipal wastewater treatment facilities in a controlled environment using anaerobic digesters. Most of these digesters are completely mixed digesters. Treatment of wastewater in municipal facilities is very expensive, and the cost is covered by charging a fee to residents or businesses for disposing off their waste in the sewer. Anaerobic treatment requires substantial quantities of heat, but this heat may be compensated for by the methane gas produced. There are many variations of anaerobic digestion that are very successful and very basic. The conversion of organic materials into biogas is performed by the microorganisms in the digester. These microorganisms do the work so long as the organic content and temperature of the digester are maintained within certain ranges.

Anaerobic filter-type reactors promote the retention of bacteria in the digester by attaching bacteria to fixed inert materials in the digester. Anaerobic filter-type digesters are also limited to primarily liquid feedstocks containing less than about 1 percent (1%) solids since they become plugged when solids concentration in the digester increases due to higher solids loading or accumulation of solids over longer periods of operation.

Horizontal plug flow digester designs have been implemented, but horizontal plug flow reactors are limited to use of homogeneous solids feed materials (such as manure), which do not tend to settle by gravity. The horizontal plug flow reactor design encourages rapid disengagement of gas from the liquid phase. Horizontal plug flow reactors generally have poor conversion efficiencies of the biodegradable fraction, on the order of about 40 to 60 percent due to biologically unreactive zones within the digester, short circuiting of the feed material, and bacterial washout.

Anaerobic digestion of terrestrial plant material to produce methane gas been recognized as exemplified by D. L. Klass and S. Ghosh, "Methane Production by Anaerobic Digestion of Bermuda Grass," presented at Symposium on Biomass as a Non-Fossil Fuel Source, ACS/Chem. Soc. of Japan Joint Chemical Congress, Honolulu, Hi., Apr. 1–6, 1979. Likewise, the anaerobic digestion of aquatic plant material to produce methane has been recognized as exemplified by R. P. Lecuier and J. H. Marten, "An Economic Assessment of Fuel Gas from Water Hyacinths," Symposium papers, Clean Fuels from Biomass, Sewage, Urban Refuse, Agricultural Wastes, Orlando, Fla., Jan. 27–30, 1976.

U.S. Pat. No. 4,329,428 teaches production of methane gas in higher yields and at higher rates by thermophilic and mesophilic anaerobic digestion of a mixture of plant material of terrestrial or aquatic origin and organic waste. U.S. Pat. No. 4,424,064 teaches production of methane gas with higher yields and at higher rates by thermophilic or mesophilic anaerobic digestion of aquatic plant material, at least a portion or all of which has been grown in organically polluted water. U.S. Pat. No. 4,316,961 teaches higher yields of methane gas at higher rates by thermophilic or mesophilic anaerobic digestion of plant material and/or organic waste of normally low biodegradability in the presence of an extract of different plant material.

An Upflow Anaerobic Sludge Blanket (UASB) process has been developed for bioconversion of feedstocks which contain primarily soluble organic waste wherein small amounts of solids, ordinarily less than 1 percent of the feedstock. The bacterial mass are allowed to settle in the reactor. The Upflow Anaerobic Sludge Blanket process and reactor are described in the following publications: G. Lettinga, et al, "Anaerobic Treatment of Methanolic Wastes," Water Research, Vol. 33, pp. 725–737, Pergamon Press Ltd. 1979; and G. Lettinga, et al, "Upflow Sludge Blanket Processes," 3rd International Symposium on Anaerobic Digestion, 1983, Cambridge Mass.; and G. Lettinga, et al, "Anaerobic Treatment of Raw Domestic Sewage" at Ambient Temperatures Using a Granular Bed UASB Reactor, Biotechnology and Bioengineering, Vol. XXV, pp. 1701–1723, 1983. This reactor design is limited to liquid feedstocks containing less than about 1 percent solids, and it requires effective gas/liquid separators, recycle for bed expansion, and means for distributing the feed over the bottom of the reactor.

Continuous flow fluidized bed fermenters embodying a tower design or a supported film reactor are described in G. F. Andrews, "Fluidized-Bed Fermenters: A Steady-State Analysis," Biotechnology and Bioengineering, Vol. XXIV, pp. 2013–2030, 1982. This article teaches that stratification tends to occur in tower fermenters, and solids concentration varies along the height of the tower fermenter, with a low cell concentration in the upper parts of the tower fermenter leading to a low volumetric productivity.

U.S. Pat. No. 4,208,279 teaches anaerobic digestion of animal waste which is fed to the top and one end of an unstirred digestion volume which is about five times as wide as it is high. Effluent sludge is removed at the opposite end of the reactor. Solids movement in the digester is essentially horizontal and the liquid volume is not agitated, except by gas formation. Suitable solids residence times are one month and over, and the solids feed concentration is about 5 percent.

U.S. Pat. No. 4,311,593 teaches anaerobic digestion of waste water in a digester volume which is about four times as wide as it is high. Microorganisms are stabilized on high surface area media. Agitation of the microorganism biomass on the media is provided by gas formation bubbling up through the reactor liquid. U.S. Pat. No. 4,388,186 teaches mechanical condensation of sludge prior to anaerobic digestion of sludge in a vertically elongated, stirred digester tank. The '186 patent also teaches conducting an acid fermentation stage and an acid regression stage separately prior to carrying put an alkaline fermentation stage in the elongated, stirred digester tank. U.S. Pat. No. 1,806,698 teaches a sludge digester wherein solids collect at the bottom. Supernatant liquid accumulating in the upper portion of the digester is recycled to the surface of the digester contents to reduce foam scum. U.S. Pat. No. 1,880,773 also teaches anaerobic digestion of sewage sludge in a digester wherein solids settle to the bottom of the tank. Liquid supernatant from the upper portion of the digester is recirculated to prevent the accumulation of scum or foam at the top surface of the digester contents.

SUMMARY OF THE INVENTION

The present invention provides both a process and apparatus for supplying one or more digesters with an appropriate feedstock for the production of usable biogas. The feedstock is a sugar, starch and/or other appropriate carbohydrate material (hereafter "feedstock") which is 10 to 100 percent (10–100%) biodegradable solids, and may be provided either as entirely new feedstock, or in combination with a waste stream. The invention uses a feedstock with a high percentage of solids in which ninety-five percent (95%) or more of the solids are biodegradable and converted into biogas. Pure sugar is an excellent feedstock as it contains over ninety-nine percent (99+%) solids and is ninety-nine percent (99+%) biodegradable. Beet molasses has a sugar base of between about forty-five percent (45%) and about forty-seven percent (47%). Such molasses will convert about ninety-five percent (95%) by weight of its sugar to biogas. Ninety-five percent (95%) of starch by weight will be converted to biogas. The balance of the sugar, starch or carbohydrate feedstock is mostly water.

Other available feedstocks include without limitation such materials as starches, high sugars (a.k.a., polysaccharides), beet sugar, sugar beet molasses, sugar beet syrup, sugar beet juice, sugar cane molasses, cane sugar, sugar cane syrup, sugar cane juice, corn syrup, glucose, cereal grains, corn flour, wheat flour, rice flour, potato juice, potato pulp, soybean sorghums, and other similar materials, and/or combinations thereof which are all feedstocks having 10 to 100 percent (10–100%) biodegradable solids. The pure sugar example above will convert the solids to 100% biogas.

It is an object of this invention with its process using anaerobic digesters will have extremely small amount of liquid waste to dispose of when not used with a wastewater treatment plant. This process converts 98 to 100 percent of its feedstock into product gas, which is a main object to this invention.

The present invention provides for the injection of large amounts of non toxic feedstock to provide uniformly high rates of bioconversion and increased process stability and profitability. Increased anaerobic digestion system stability results in production of higher quality product gas having a higher methane content, and more efficient utilization of feedstock. Valves and/or pumps utilized in the practice of the present invention are located externally of the digester contents, and may be replaced if needed, requiring little or no digester downtime. The present invention provides substantially complete bioconversion of biodegradable components of feedstocks and a higher bioconversion of wastewater biosolids in standard municipal wastewater treatment plants due to the extremely high concentration of thermophilic microorganisms and methanogenic organisms that are developed and retained in the digesters. The present invention provides substantially complete bioconversion of biodegradable components of feedstocks at enhanced bioconversion rates.

The process of the present invention includes the basic steps of determining the appropriate feedstock(s) to be used, supplying one or more such feedstocks to at least one digester either as entirely new feedstock or mixed with waste water to form an input stream, and recirculating the stream through a thermophilic anaerobic digester and then a mesophilic anaerobic digester operated in a series. The content of the input stream as well as the temperature of each of the digesters must be carefully established and monitored during the conversion process. The process may include the additional steps of preheating the input stream (particularly when entirely new feedstock is used), and scrubbing the biogas produced from the reaction for more refined uses.

The process will be able to work a single digester or a series of several digesters of the complete mixed digesters type. The process and apparatus work in a variety of shaped tanks. The inside of the digester tanks contain no moving parts. The anaerobic digestion process and apparatus of the present invention allow two to ten times greater solid loads than conventionally used continuously stirred tank digesters, thus providing lower digestion volume requirements per pound of solids converted to useful gas. Conventional stirred tank digesters operating under mesophilic condition accommodate solids loading of about 0.05 to about 0.1 lbs. organic matter/ft$^3$/day. The solids concentrating thermophilic anaerobic digestion process and apparatus of the present invention operates a much higher solids loading in excess of 3.0 lbs. organic matter/ft$^3$/day under loading of sugar, starch or carbohydrates. The less sludge entering the digester the more sugar that may be applied and the more gas produced. The advantage of sugar-fed anaerobic digesters is the temperature, which will be controlled at 70° C. or higher when used with municipal sewage waste water treatment plants, and will retain greater system stability. The hydrolysis fermentation microbial population is relatively resistant to contaminants and toxic components while the methane-producing microorganisms have a lower resistance to toxic components.

The apparatus includes at least one, but preferably two, anaerobic digesters operated in series, an appropriate feedstock collection and conveyance system such as a drop tank or the like, piping, tubing, valves, temperature controls, heaters and scrubbers. In particular, the apparatus includes piping and holding tanks for injecting metered, controlled feedstocks such as sugar beet molasses or sugar cane molasses into the mixing line of the thermophilic digester so that the input comes out at the top liquid level in the thermophilic digester and mesophilic digester. The apparatus reduces or eliminates scum formation by recycling a portion of the digester contents continually and returning the contents to the top of the liquid level of the digester.

In particular, the mixing/recirculating line of the digester has an external pump that draws the slurry from the bottom of the digester and pumps the slurry to the top of the slurry level of the digester near the top, this pumping method makes the digester completely mixed at all times. New feedstock having a suspended solids concentration of between about 10 to 100 percent biodegradable solids is introduced into the recirculating mixing line, and is diluted immediately with the digesters slurry and enters the digester at the top. Normal wastewater treatment plants have very low solids coming into the plant. The primary and secondary sludge is controlled as to the desired solids content of the digester. Said control of desired solids allows the operator to add an appropriate amount of sugar, starch and/or carbohydrate feedstock in order to create very active thermophilic and mesophilic digesters.

At least two very different systems are provided by the present invention. The first is a stand-alone system for production of biogas that utilizes an input stream containing a carefully selected and closely monitored feedstock mixed only with water and/or the existing digester slurry. The second is an add-on (retrofit) system to an existing waste stream (such as is found in a municipal waste water treatment facility) for improving the quality of the existing waste stream for better production of biogas and higher percentage of conversion of biodegradable solids in the waste stream.

The primary object of this invention is to efficiently create the maximum amount of biogas for the least amount of cost.

The first aspect of the invention is the stand-alone system which utilizes both a thermophilic anaerobic digester and a mesophilic anaerobic digester that operate with a controlled feedstock of 10% to 100% organic biodegradable solids. The feedstock must be highly biodegradable and use only enough water to form a slurry for mixing purposes. The stand-alone system does not use any waste products nor is it used in conjunction with any wastewater or sewage treatment plant of any kind. The digesters in the system each have an active, producing microbial anaerobic digestion population comprising hydrolysis fermentation organisms suspended in liquid. In the stand-alone system, the feedstock may be sugar, starch, carbohydrates, or any combination of them, and should preferably contain between ninety and one hundred percent (90%–100%) solids that are substantially fully biodegradable (i.e. approaching ninety-nine percent 99% biodegradable). Once the digesters are started, the feedstock is mixed and then carefully introduced into the digesters in series where it is digested and becomes biogas.

The stand-alone system provides virtually complete (i.e. approaching 100%) bioconversion of biodegradable solids. As a result, some non-contaminated water added to dilute the feedstock must be used to keep the digester at an acceptable level for the process to continue. The biogas produced is wet as it rises and is drawn off the top of the inside of each digester. Because the stand-alone system uses non-toxic, organic, highly biodegradable feedstock with low water content, there is little, if any, washout of feedstocks and microorganisms, thus resulting in increased conversion efficiency and more stable digester condition.

It is therefore an important object of the stand-alone system to create very little effluent to dispose of, make higher biogas production and have no biosolids to dispose.

It is also an important object of the stand-alone system to provide unlimited retention time as the feedstock stays in each digester until it comes out as biogas.

It is also an object of the stand-alone system to provide a process and apparatus for anaerobic digestion of feedstocks of sugar, starch and carbohydrates in a totally newly constructed, free standing facility built for the sole purpose of creating biogas from a renewable product and not using a waste product or being used in conjunction with a waste water treatment plant receiving sewage from a city.

It is an object of the stand-alone system to use dry feedstocks such as sugar, starches and carbohydrates that will be mixed with either non-contaminated water or digester liquid to create a slurry needed for ease of pumping.

It is an object of the stand-alone system to avoid the need for higher temperatures otherwise necessary to pasteurize the pathogens and other contaminants found in a waste stream. In a stand-alone digester/biogas plant, after all of the solids have been converted to gas there will be little if any remaining waste to dispose of.

In another aspect of the invention, an appropriately selected feedstock concentration is mixed with a waste stream and then introduced into the digester(s) for conversion into biogas. Combining the system with a municipal or other waste water treatment facility will help to create a high volume of biogas which is profitable to sell, while also helping the facility to attain the Class A biosolids 40 C.F.R. Part 503 Standard by pasteurizing sewage sludge.

One of the main costs in producing methane gas is the cost of building the digester. In the case of municipal wastewater treatment plants, many thousands of sites the world over are existing, and have been built at a cost of hundreds of thousands and many in the hundreds of millions of dollars. With the treatment plants in place and no dollar return ever, all are non-profit due to the fact that they were never built to create an income. They were built solely to treat wastewater for the safety of the environment. With the process and apparatus of this invention, the digesters will produce very large amounts of methane, which will return a profit on additional money invested. The gas produced can be used in many ways. The gas can be used straight as biogas in the boiler for steam or electric cogeneration. Scrubbing the biogas to clean methane gas and pressurizing the clean gas and pumping to storage tanks allows for sales to the public in place of natural gas.

It is an object of the process and apparatus of the present invention to create an economical and profitable anaerobic digester from very large amounts of gas generated by the controlled feeding of a non-toxic biodegradable sugar or starch feedstock such as starches, high sugars, (a.k.a., polysaccharides), beet sugar, sugar beet molasses, sugar beet syrup, sugar beet juice, sugar cane molasses, cane sugar, sugar cane syrup, sugar cane juice, corn syrup, glucose, the starch group of cereal grains, oat flour, rice flour, corn flour, wheat flour, potato juice, potato pulp, sorghum, and other similar materials, and/or combinations thereof, all of which are hereinafter referred to as "feedstocks".

It is an object of this invention to enhance existing municipal wastewater sewage treatment plants and digesters and to provide substantially complete bioconversion of biodegradable components of biomass and organic waste materials to usable product gas.

It is an object of this invention to be able to add this process to any existing municipal wastewater treatment plant or other similar facility, and to create a return on the investment therein resulting from the cost of such things as tanks, pumps, compressors and feedstock required by the addition.

It is an object of this invention to aid municipal wastewater treatment plants in meeting the fecal coliform requirements of the recent 40 C.F.R. Part 503 Standards for Class A biosolids through the pasteurization capability of the thermophilic digester.

It is an object of the present invention to produce all the electric and gas needs of the treatment plant and have excess power and gas to sell to outside markets.

It is an object of the present invention to teach municipal wastewater treatment plants how to produce methane gas in higher yields and at higher rates by thermophilic and mesophilic anaerobic digestion by adding extra feedstock, such as sugars, starches and carbohydrates, in existing treatment plant digesters.

It is an object of the present invention to teach the production of clean burning gas which is made from renewable non toxic organic materials like corn syrup, corn flour, wheat flour, potatoes, sugar beet syrup, sugar beet molasses, sugar cane juice, syrup and molasses.

It is an object of the present invention to teach the production of clean burning gas which is made from renewable non toxic organic materials like sugar, starch and carbohydrates.

It is an object of the present invention to teach the use of scrubbing biogas to create a salable gas product (i.e. methane) that may be used to operate any existing truck, bus, auto or farm engine which is now running on natural gas with little or no adjustment.

It is another object of the present invention to utilize any unscrubbed biogas by burning it in a gas fired boiler to create the steam needed in the wastewater treatment plant for such diverse uses as heating digesters, molasses tanks and pipes; for steam turbines to generate electricity; for heat exchangers for the plant use, and/or to generate and sell excess power to the local power company in the area.

It is another object of the present invention to create a large demand for sugar beet molasses and cane molasses or sugar beet juice, cane juice, corn flour and wheat flour in order to create a larger demand so as to enable the farmers to produce and market a larger supply of feedstock.

It is an object of the invention to improve most wastewater treatment plants through a two-stage digester system, one a thermophilic and the other a mesophilic digester.

It is yet another object of the invention to successfully use high solid concentrations of sugar, starch and/or carbohydrates in a thermophilic or a mesophilic anaerobic digester apart from any wastewater treatment facility in a profitable manner.

It is an object to this invention to use a process of high biodegradable solids such as sugar or sugar beet molasses and cane molasses and starches.

Beet molasses is one example of the type of feedstock that is described in this invention. A brief analysis from BSK Analytical Laboratories, Fresno, Calif., of a solid sample of beet molasses is shown in the following tables:

TABLE 1

Analysis of Beet Molasses (solid sample) (sampled 9/1/2000)

| Analyte | Method | Result | Units | PQL | Dilution | DLR | Prep Date | Analysis Date | |
|---|---|---|---|---|---|---|---|---|---|
| BOD | SM 5210-B | 380000 | Mg/Kg | 50 | 1000 | 50000 | 09/07/2000 | 09/12/2000 | H |
| COD | SM 5220-D | 690000 | Mg/Kg | 50 | 1000 | 50000 | 09/07/2000 | 09/07/2000 | |
| pH - DI Extract | EPA 9040 | 9.1 | Std. Unit | — | 1 | N/A | 09/07/2000 | 09/07/2000 | |
| Solids | SM 2540-B | 98 | % | 0.1 | 1 | 0.1 | 09/08/2000 | 09/11/2000 | |
| Volatile Solids | SM 2540-B | 100 | % | 0.1 | 1 | 0.1 | 09/18/2000 | 09/20/2000 | H |

BOD - biochemical oxygen demand
COD - chemical oxygen demand
PQL - practical quantitation limit
DLR - detection limit for reporting: PQL × Dilution
H - analyzed outside of hold time

TABLE 2

Analysis of Sugar (Solid Sample) (sampled 1/12/2001)

| Analyte | Method | Result | Units | PQL | Dilution | DLR | Prep Date | Analysis Date |
|---|---|---|---|---|---|---|---|---|
| BOD | SM 5210-B | 520000 | Mg/Kg | 50 | 2000 | 100000 | 1/12/2001 | 01/17/2001 |
| pH - DI Extract | EPA 9040 | 4.7 | Std. Unit | — | 1 | N/A | 1/15/2001 | 01/15/2001 |
| Solids | SM 2540-B | 100 | % | 0.1 | 1 | 0.1 | 1/16/2001 | 01/19/2001 |
| Volatile Solids | SM 2540-B | 100 | % | 0.1 | 1 | 0.1 | 1/16/2001 | 01/19/2001 |

BRIEF DESCRIPTION OF THE SEVERAL VIEWS OF THE DRAWINGS

These and attributes of the invention will become more clear upon a thorough study of the following description of the best mode for carrying out the invention, particularly when received in conjunction with the drawings, wherein.

DETAILED DESCRIPTION OF THE INVENTION

Figure 1:
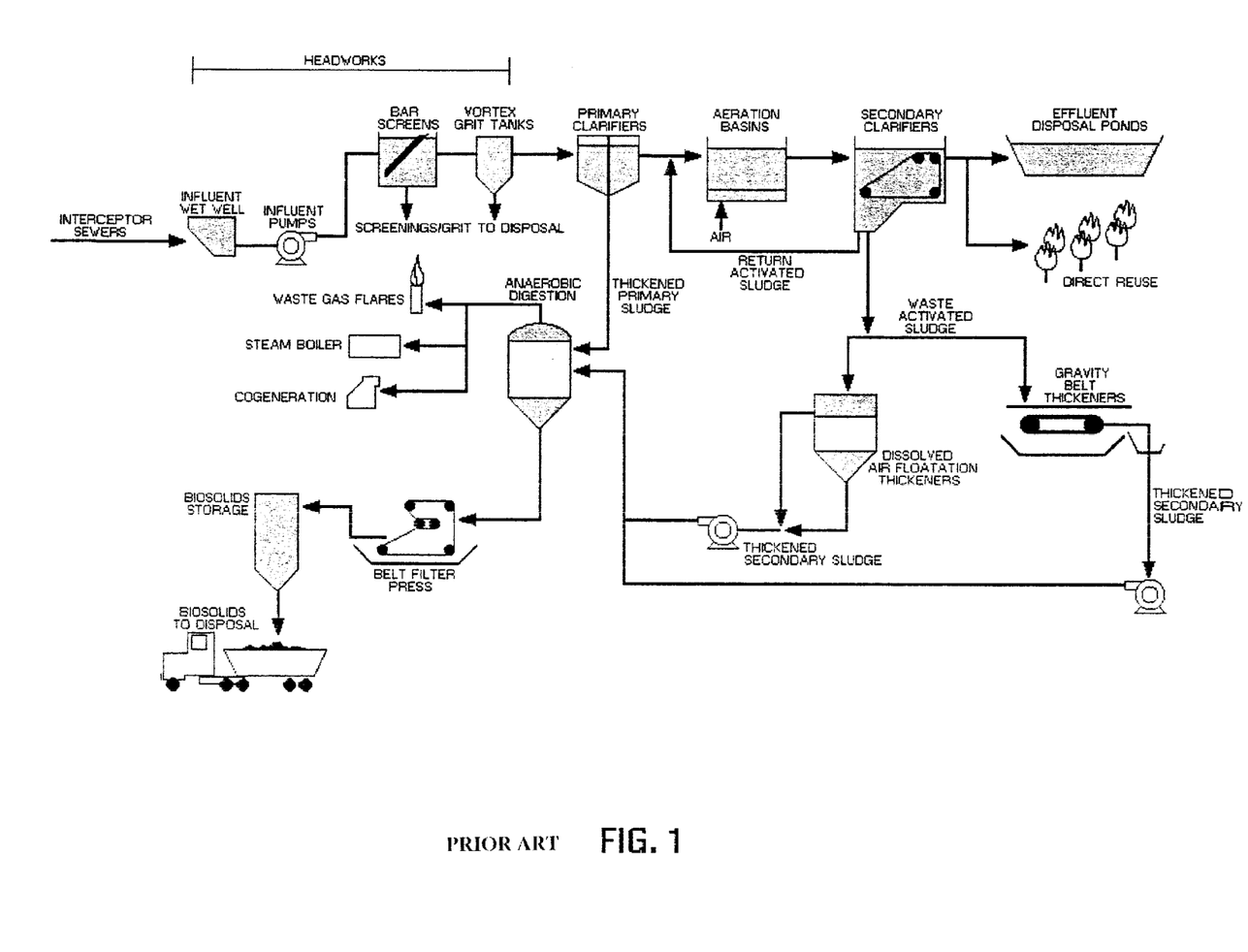
FIG. 1 is a flow scheme of a typical prior art wastewater plant.

FIG. 1 is a flow scheme according a typical prior art wastewater treatment plant.

Figure 2:
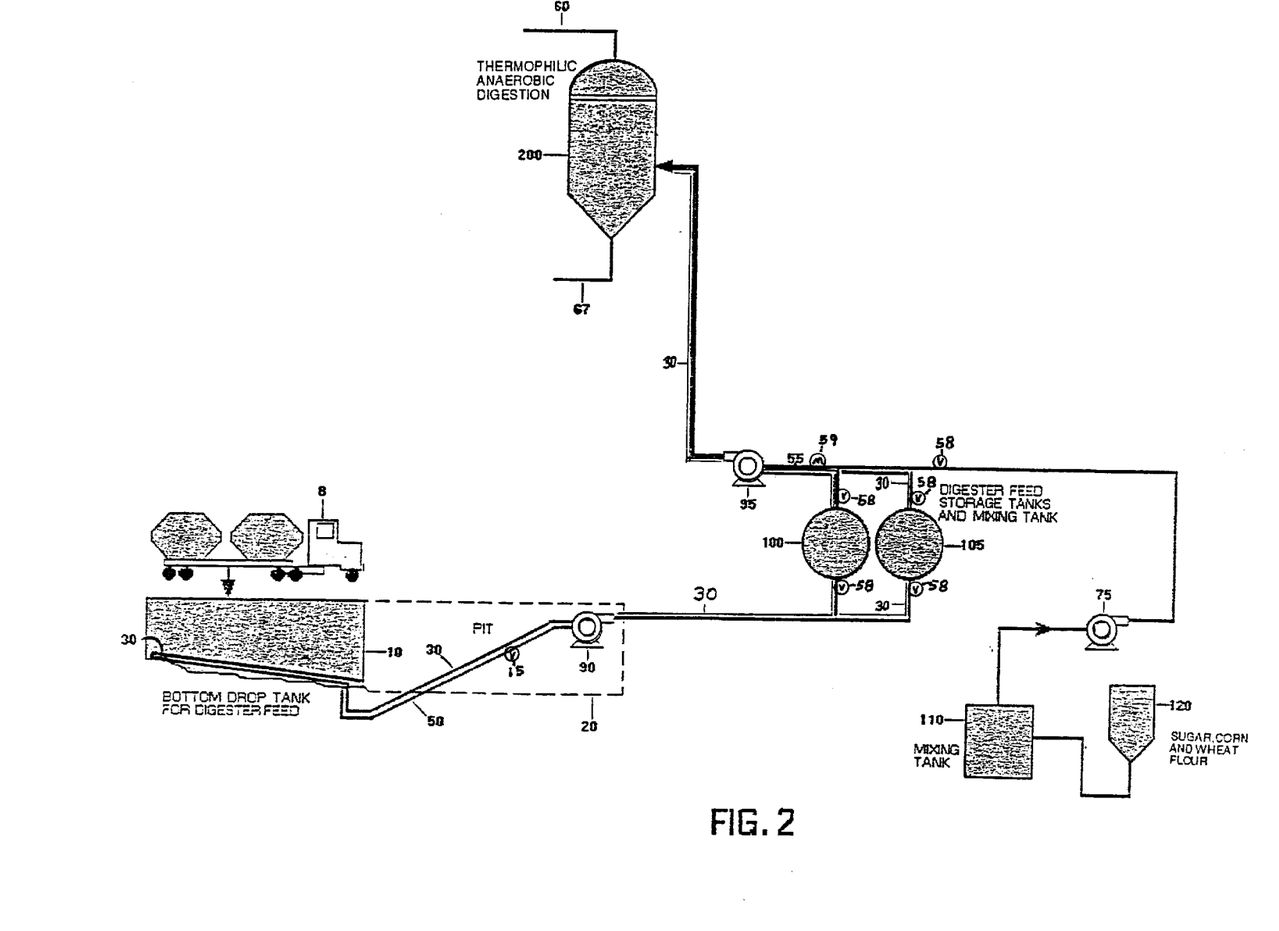
FIG. 2 is the first portion of a flow scheme according to the present invention.

In FIG. 2, the process and apparatus of present invention reveals a buried drop tank 10. In this particular example, the top of tank 10 is level to the ground surface; however, it could be higher or lower. Drop tank 10 is in line with a driveway for incoming traffic so that a large vehicle 8 may drive over tank 10 to drop the incoming feedstock (such as sugar cane molasses, sugar beet molasses, and/or any new feedstock) that is in slurry form in order to be able to be pumped to feed the digesters in order to obtain high production of methane gas. The bottom of tank 10 is positioned where one end of the tank 10 is lower than the other so the feedstock will flow to the lower end of tank 10. There is an outlet pipe 50 at the lower end of tank 10, and a valve 15 connected to pipe 50 to regulate the transfer of feedstock out of tank 10. The transfer is accomplished by pumping with a viscosity rated pump 90 to the slurry storage and mixing feedstock tanks 100 and 105, respectively.

Inside of drop tank 10 there is a small pipe 30 running the entire length of the bottom of the tank. Circulating hot water is constantly provided in pipe 30 to work as a heat exchanger to keep the feedstock warm so that it may be pumped more easily. The heat exchanger pipe 30 lies on the bottom of said drop tank 10 and extends out along the transfer pipe 50 into the storage feedstock and mixing tanks 100 and 105.

The feedstock slurry storage tanks 100 and 105 shown in FIG. 2 are sized according to the anticipated amount of feedstock to be supplied. Separate additional tanks 110 and 120 may be provided as storage and as mixing tanks for corn flour, wheat flour or other dry starch/carbohydrates that would need water to be added to form a slurry before pumping into the thermophilic digester 200. The feedstock slurry storage tanks 100 and 105 have an outlet pipe 55 connected by a valve 58 and a viscosity pump 95 with a meter 59 to control the flow. Heat exchange pipe 30 extends along pipe 55 to the digesters to keep the feedstock warm and flowing. The amount of feedstock fed into the thermophilic digester 200 is regulated using meter 59 in order to keep a well-balanced digester. At all times the digester needs to have a pH reading of between about 6.7 and about 7.8, with a pH of about 7 optimum.

Figure 3:
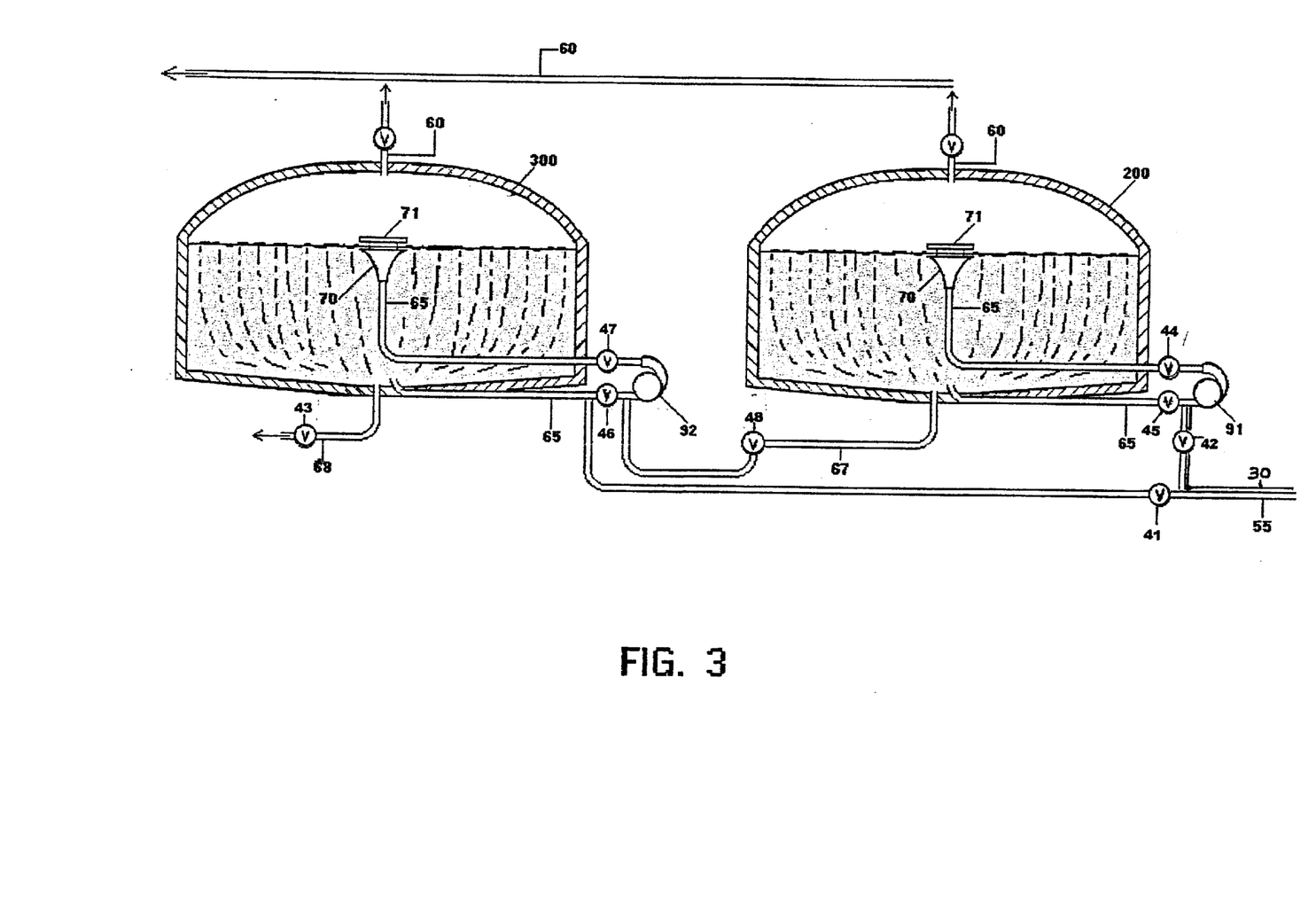
FIG. 3 is a side sectional view showing an example of the digester/mixing/re-circulating, pipe and scum remover of the present invention.
Figure 4:
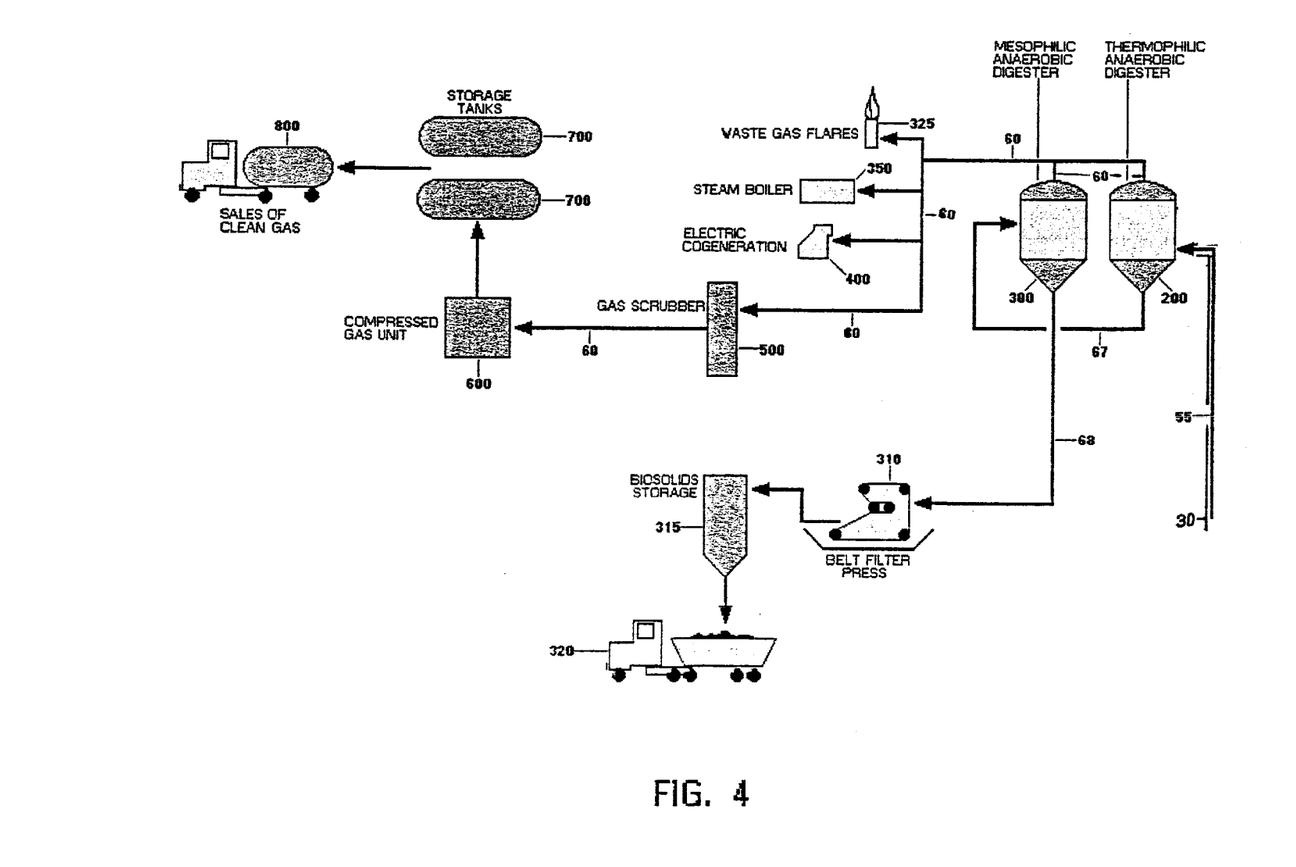
FIG. 4 is the second portion of a flow scheme according the present invention.

FIG. 3 is a cut away view of the thermophilic digester 200 and the mesophilic digester 300. A gas pipe 60 is provided at the top of the dome of each digester 200 and 300. Gas produced inside each digester is piped to one of four locations as shown in FIG. 4: to the gas scrubber 500; to the cogeneration unit 400; to the steam boiler 350; or as a last resort, to flare pipe 325 which is always burning.

The pumps 91 and 92 and valves 41–47 and 48 (shown in FIG. 3) are placed such that the pumps 91 and 92 draw off the bottom of digesters 200 and 300, respectively. Valves 41 and 42 are used to control whether the input from pipe 55 flows to the thermophilic digester 200 or the mesophilic digester 300. In digester 200, valves 44 and 45 are used to control the circulation of material in the digester using pump 91. By opening valve 45 and 46, material is drawn from the bottom of the digester for re-circulation. By opening valve 42, fresh feedstock is introduced into digester 200. The same valve configuration is used in the mesophilic digester 300 using pump 92 and valves 46 and 47. By opening valve 41, fresh feedstock is introduced into digester 300. Valve 48 allows the mesophilic digester 300 to draw from the thermophilic digester 200 through pipe 67. By adjusting valves 41–48, a host of different mixtures of materials are possible.

The biodegradable solids that have not yet been digested and converted into biogas settle on the bottom of the digesters 200 and 300 where the digester liquid and heavy solids are settling. The solids and sludge are then drawn from the bottom of each digester through pipe 65 where additional sugar/feedstock may be injected through valves 41 or 42 using pumps 91 or 92 to mix the feedstock and re-circulate it back to the top of the digesters. Pumps 91 and 92 discharge the liquid sludge at the top of the digesters 200 and 300.

In each digester a funnel shaped outlet 70 is provided at the top of the discharge pipe 65, and has a round steel plate 71 the same size as the perimeter of the top of funnel 70. Pipe 60 is attached higher than the funnel to prevent any liquid from splashing into the gas vent pipe 60. Also, plate 71 acts as a liquid spreader and scum preventer as the slurry is spread out evenly across the top of digesters 200 and 300. The interaction of funnel 70 and plate 71 discharges the liquid/sludge out in a rapid rolling motion and ripples across the top of the digester liquid. In this process the flow spreads out evenly to the outer walls of the tanks 200 and 300 and prevents any scum from being formed. The even spread of the re-circulating digester liquid/sludge promotes a very high content of the active producing microbial anaerobic digestion population comprising hydrolysis fermentation organisms. Such a high content of organisms also has all the available nutrients, and the organic feed, which has a greater chance to digest the biodegradable solids and convert them to biogas.

The present invention provides an apparatus to create a thermophilic anaerobic digester 200 that is a high solids fed digester. The solids content in the digester could exceed fifteen percent (15%), with five percent (5%) as sludge and the remaining ten percent (10%) coming from the non-toxic feedstock of sugar beet molasses, or the like. The sludge is a factor that will be controlled when using this invention with a municipal waste water system of sewage waste. Effluent coming into the waste water sewage systems has a solids content of one to two percent (1–2%) when first coming into the treatment plant, after bar screens, grit tanks, clarifiers and thickened secondary sludge, the solids percentage becomes much higher. When the water is sent to disposal ponds the heavy sludge is sent to the digester for treatment. If, for example, ten percent (10%) by volume of sugar feedstock is added in the re-circulating/mixing line 65, the digesters population of hydrolyzing anaerobic fermentation organisms are greatly increased due to the added feedstock which becomes 98% to 100% biodegradable in a matter of hours, due to the increased number of anaerobes. The sewage sludge that is biodegradable will also be converted to biogas more quickly.

In a stand-alone biogas producing plant digester, the solids content in the digester could be fifteen percent of solids which are ninety-eight to one hundred percent biodegradable solids, such as pure sugar (100% solids) or cane molasses which is approximately forty-seven percent sugar and has approximately ninety-eight percent solids.

In a stand-alone biogas plant (without sewage treatment), there is very little effluent to dispose of. All of the solids are converted to biogas. Non-contaminated water or well water is needed only to dilute the solids being fed into the digester. Some of the digester liquid could also be used to mix first with the feedstock and then be metered into the mixing line 65. The thermophilic anaerobes in the high state of digestion will have a higher count of acid forming bacteria and methane producing organisms. As effluent substrate concentration increases, the efficiency of any biological process improves. Also, as effluent concentration increases, reactor loadings can be increased within limits while maintaining a suitable hydraulic retention time (HRT). In anaerobic treatment this means a larger output of methane per unit volume of reactor per unit time.

In FIG. 3 the thermophilic digesters 200 liquid sludge may be pumped from the bottom line 67 and pumped into the mesophilic digester 300. The mesophilic digester is not heated other than from the waste thermophilic digester 200. In the mesophilic digester 300 with the lower temperature, the new feedstock of beet molasses and sugars, starches, etc., will be fed at a lower rate. This is to be a finishing digester in order to complete the conversion of any biodegradable solids left from the initial thermophilic digester 200 in FIG. 5 of the stand alone biogas plant using only feedstocks that are highly biodegradable ninety-eight to one hundred percent solid, sugar, starch and carbohydrates only, not connected to any municipal wastewater sewage treatment plant.

The stand-alone biogas plant does not need a lot of equipment that waste water treatment plants need such as clarifiers, dissolved air floatation thickeners and belt filters process due to the fact the stand alone biogas plant converts approximately ninety-nine percent of its feedstock to biogas. In a municipal waster water sewage treatment plant the digester 300 is a finishing digester also. The mesophilic digester 300 is built and operated the same as the thermophilic digester 200. The final draw of sludge is pumped from the bottom line of said digester 300 and pumped to the belt filter 310 as shown in FIG. 4.

In FIG. 4 is a flow scheme showing the digesters 200 and 300 from FIG. 3 and the flow of digested gas discharged from the digesters 200 and 300 through pipe 60. The gas is transferred to a digested gas co-generating unit 400 and used as an energy source thereof to generate electric power. In addition, steam or hot water generated in the generating unit 400 is used as a heat source for heat treatment for maintaining the high temperature of the thermophilic digester 200 and heated water in pipe 30 to maintain the fluidity of the feedstock in the drop tank 10 and the storage tanks 100 and 105 shown in FIG. 2. The heated water circulating will serve as the circulating water to heat the feedstock pipelines 50 and 55.

FIG. 4 shows a flow scheme of gas discharged through pipe 60 from the digesters 200 and 300 and transferred to a boiler 350 for steam, if needed. The flow scheme also shows the gas discharged from the digesters through pipe 60 to a gas scrubber 500 which is then pressurized with a high pressure gas unit 600 and stored in large pressurized gas tanks 700 of the common propane tank type. The gas from this point is transferred to pressurized tanks 800 on trucks and delivered to the end users such as farmers who use propane to run engines that power their water well pumps and many other engines. Said gas, after scrubbing, can be used in any natural gas vehicle (i.e. bus, truck, auto, forklift, etc.). In FIG. 4 the sludge coming out of the mesophilic digester 300 is piped to the belt filter 310 and the biosolids storage tank 315. The biosolid is loaded onto trucks 320 and sold as fertilizer and compost, since these biosolids meet the recent 40 C.F.R. Part 503 Standard. Pasteurization is achieved by retaining the solids or slurry for 30 minutes or more at 70° C. or higher.

Figure 5:
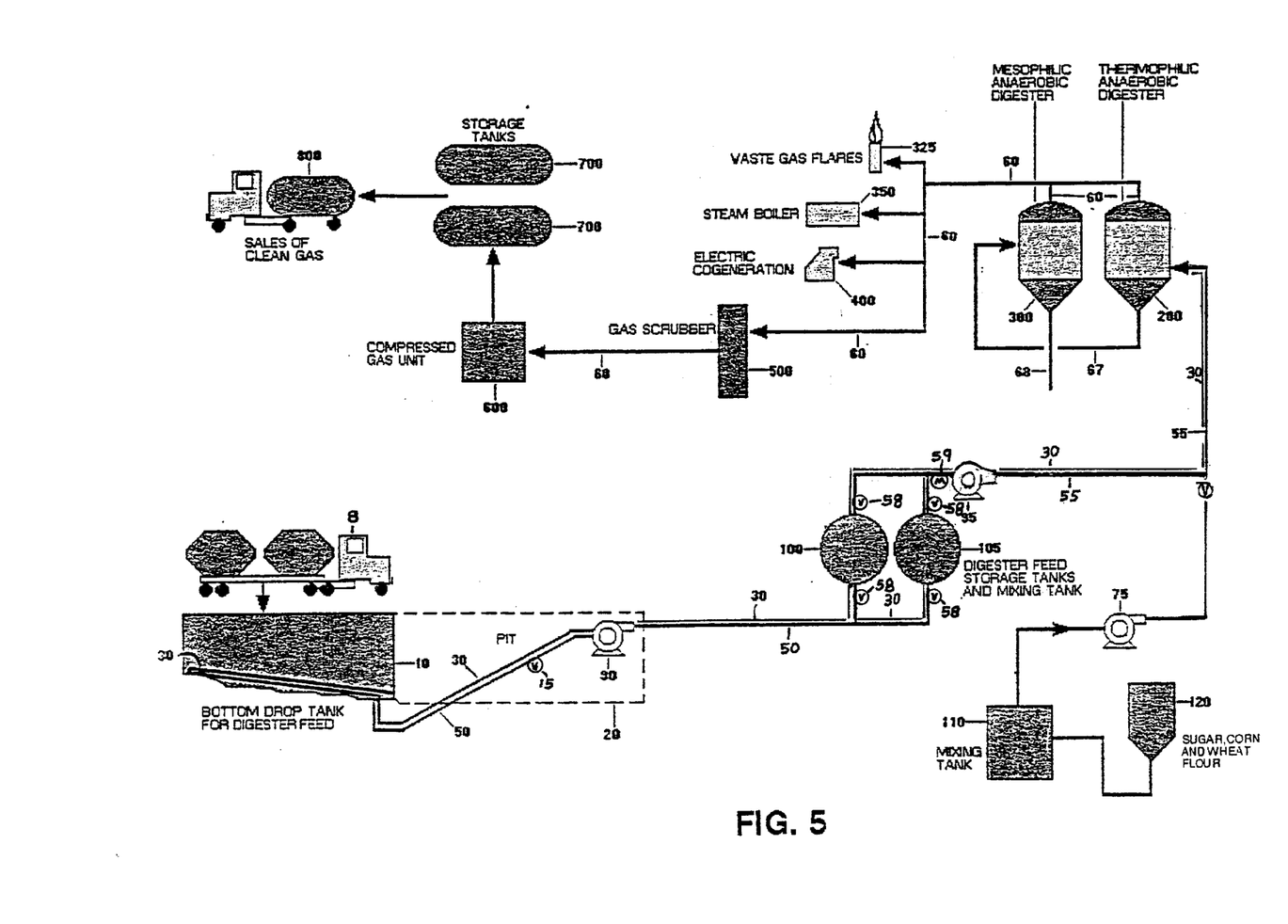
FIG. 5 is the stand-alone portion of an alternative flow scheme according to the present invention.

In FIG. 5 is a flow scheme of a sugar/starch plant that is not part of any wastewater system showing the digesters 200 and 300 from FIG. 3. The digested gas discharged from the digesters 200 and 300 is transferred to a digested gas co-generating unit 400 and used as an energy source thereof to generate electric power. In addition, steam or hot water generated in the generating unit 400 is used as a heat source for heat treatment for maintaining the high temperature of the thermophilic digester 200 and heated hot water line 30 to maintain the storage feedstock tanks 100 and 105 in FIG. 2. The heated water pipe 30 will serve as the circulating water to heat the pipelines 50 and 55. FIG. 5 shows a flow scheme of gas discharged through pipe 60 from the digesters 200 and 300 and transferred to a boiler 350 for steam, if needed. The flow scheme also shows the gas discharged from the digesters through pipe 60 to a gas scrubber 500 and then pressurized with a high pressure gas unit 600 and stored in large pressurized gas tanks 700 of the common propane tank type. The gas from this point is transferred to pressurized tanks 800 on trucks and delivered to the end users such as farmers who use propane to run engines that power their water well pumps. Said gas, after scrubbing, can be used in any natural gas vehicle (i.e. bus, truck, auto, forklift, etc.). In FIG. 5 the miniscule amount of effluent, if any, coming out of the mesophilic digester 300 is transferred through pipe 68 to an irrigation pipeline and mixed with irrigation water which may then be used on crops when used on a farm, or into a sewer line when built in an urban area.

Temperature ranges for the thermophilic digester should be between about 37.8° C. and about 97° C., with a preferred range of about 40° C. to about 60° C., and an optimum temperature of 50–55. Similarly, temperature ranges for the mesophilic digester should be between 21° C. and about 40° C., with an optimum temperature of about 30–35° C. The preferred hydraulic retention time in the thermophilic digester is between about 1 and about 8 days and the preferred hydraulic retention time in the mesophilic digester is between about 4 and about 15 days.

Example of a Working Stand-Alone System

With regard to biogas production as it is normally done today, the stand-alone facility is a very unique approach. A stand-alone facility will consist of one or more digesters. It can be only a thermophilic anaerobic digester, or only a mesophilic anaerobic digester, or it can be a one of each, a thermophilic anaerobic and a mesophilic anaerobic digester, or several, depending on the design of the electrical generating facility that one wishes to build. The thermophilic temperature range of 50° to 55° C. is optimum; therefore, the thermophilic temperature should be maintained at around 50° C., and 35° C. for the mesophilic stand-alone digester. Many studies show a peculiar pattern: when the hydraulic retention time (HRT) is decreased and the loading rate is increased, the percent of volatile solids (VS) destruction goes up.

In the stand-alone digester the loading rate is increased from 1–1,000% more than the sewage waste loading rate in a normal wastewater treatment plant. The VS destruction is up to 100% due to the fact that the feedstock fed into the digester is up to 100% biodegradable. The only water content added is to control the level of the digester. The digester slurry is used to dilute the feedstock being metered into the recirculating line of the digester. This means that the feedstock put in comes out as biogas. The HRT is continued for several days or months until the point where all of the feedstock is converted to biogas. There is very little, if any, wash out of sugar or microorganisms due to the fact that there is very little effluent to dispose of.

Sugar Conversion To Biogas/Electricity/Money
(Stand-Alone System)

By way of example for illustrative purposes only, and without limiting the scope of the appended claims, the following assumptions and calculations are set forth to demonstrate the utility, efficiency and productivity of a stand-alone digester system.

Adjustments and Definitions. A substrate high in sugar can be expected to have an acid tendency, so a buffer would be added. In most biological processes, the rate of methane production virtually doubles for every 18–27° F. (10–15° C.) rise in temperature. If pH drops, calcium carbonate (CaCO3, commonly called "lime") can be added to return pH to the percentage it must maintain. Ammonia (NH3) is toxic to the biogas creation process in too great a concentration, however, small amounts of ammonia will correct an acid condition in a digester. An acid pH can be corrected by using one part by volume of ammonia mixed with 40 parts by volume of warm water for every 10.000 p parts by volume of generator volume. Nutritional balance and pH adjustments may be made to the digester systems as necessary, a fact known in the art, to optimize the biogas production.

C/N=Carbon to Nitrogen ratio

NH3=Ammonia (the molecule) is toxic to the biogas process in too great a concentration NH4+—Ammonium—the ion BOD—biochemical oxygen demand COD—chemical oxygen demand Temperature. Mesophilic bacteria: 21° to 40° C., with 30° to 35° C. optimum (70° to 105° F.); thermophilic bacteria: 40° to 60° C., with 50° to 55° C. optimum (104° to 140° F.). It is to be noted that thermophilic organisms do survive at mesophilic (20° to 40° C.) temperatures, while mesophilic organisms generally cannot survive thermophilic temperatures.

Assumptions. Analysis of sugar=780,000 mg/kg COD, (78 weight %)=520,000 mg/kg BOD (52 weight %). Ratio 1.5×BOD=COD. Therefore: 1 lb. of sugar is equal to 0.78 lbs. of COD, or 0.52 lbs. of BOD. One pound of COD reduced to gas in a digestion system yields approximately 20 cubic feet of biogas. Biogas is approximately 70% methane. One cubic foot of methane is equal to 980 BTU's. A digestion system can reduce approximately 95–99% of the COD fed to gas. It is reasonable to assume that sugar would be approximately 98% reduced in a system.

Calculations

Biogas produced from 1 lb. of sugar=1 (lb. sugar)×0.78 (%COD)×0.98 (% reduced)×20 cubic ft./lb. reduced=15.29 cubic feet of biogas per one lb. of sugar fed to the digester.

Assume a generator requires approximately 12,500 BTU's to produce one kilowatt (kwh) of electricity. This is known as "heat rate" in the generator trade, the actual number depending upon the generator selected. BTU's produced=15.29 (cu. ft. of biogas)×0.7 (% methane)×980 BTU's/cu.-ft.=10,489 kwh produced=10,704.7/12,500=0.84 kwh per pound of sugar fed to the digester.

Economics: California electrical generation plants sell electricity at peak times from $0.10 to $1.10 per kwh. If a kilowatt hour is worth 10 cents, then the 1 lb. of sugar, reduced to gas is worth 10×0.84 or 8.4 cents, or 92.4 cents per lb. of sugar, when the price is $1.10 kwh or more depending on supply and demand of electricity. The State of California has recently paid as much as $3.00 per kwh.

Conclusions/Benefits: The outstanding qualities of the stand-alone digester are as follows:

A. Renewable Electricity Generation

B. Cost Competitiveness

C. Non-fossil Fuel

D. Reliability

E. Dispatchability

F. Power Quality

G. Safety

H. Non-energy Benefits (agriculture and sugar industries)

I. Innovation

J. Storability

K. Availability

The stand-alone facility is cost competitive in a deregulated electricity market, whereas most renewable energy facilities are not.

Using sugar, starch and carbohydrates in the stand-alone facility for renewable electricity generation offers the same degree of reliability and dispatchability as compared to existing fossil fuel generation systems. Sugar, starch and carbohydrates can be more safely and easily stored and are far safer environmentally than storing fossil fuels.

One of the important attributes of the stand-alone digester is the fact that the biogas is available on demand just as is the case with fossil fuels. If there is a high demand for electricity in an area for a certain time period, say from 1:00 p.m.–5:00 p.m. on a Tuesday afternoon, where there is an existing stand-alone facility, the stand-alone facility could increase it's capacity to meet this period of demand. The stand-alone digester could be operating at a low, 10%–15% capacity, until 11:30 a.m. on Tuesday morning. Then, by increasing the sugar feedstock, the desired increased amount of biogas would be available to meet the 1:00 p.m. need. This production increase can range from 20% to 100% of the capability of the stand-alone digester within 1½ hours. This underscores the fact that a stand-alone digester will produce a reliable amount of electricity, thus allowing the systems to effectively and efficiently provide peak power that economically equals that of fossil fueled electricity generators.

The stand-alone, non-toxic, renewable energy digesters will have the ability to integrate into existing environments or structures and have far reaching non-energy related benefits including the development of new farmland and the creation of new jobs in the sugar/agriculture industry.

The stand-alone digester uses only a controlled, metered, non-toxic feedstock, such as sugar, starch or a carbohydrate. Unlike sewage waste treatment plants which receive a waste stream that contains hidden antibiotics, disinfectants and cleaning agents and also varies between uncontrollable high and low volume feeds, the stand-alone digester is strictly controlled and will perform on command by the operator.

EXAMPLE OF A WASTEWATER TREATMENT PLANT

By way of example for illustrative purposes only, and without limiting the scope of the appended claims, the following assumptions and calculations are set forth to demonstrate the utility, efficiency and productivity of the digester system of the present invention when coupled with an existing wastewater treatment facility. The process and apparatus of this invention when used with a wastewater treatment plant will enhance the conversion of the biodegradable solids an additional 25% over and above the normal conversion of about 50%. The rate of conversion of solids to biogas means 25% less solids to handle and more biogas created to generate more electricity.

The process is the same as the stand-alone digester process where the sugar feedstock is at all times controlled by a meter and fed the amount of feedstock as required to create the desired amount of biogas to operate the gas fired generator at a specific time. The wastewater treatment plant normally would have enough nutrients in the incoming waste so that no additional nutrients would be required. The digestion process would maintain a pH of about 7.

The return on investment when using sugar/feedstocks will increase when used with a wastewater treatment plant. The conversion of biodegradable sludge will increase to 75%, which is a 50% increase from the normal conversion amount of only one-half of the biodegradable sludge of most wastewater treatment plants due to the following reasons. The wastewater facility will increase the conversion of its biodegradable solids to biogas by about 50% by having sugar, starch or a carbohydrate added to its existing digesters in order to create a much higher population of microorganisms that will increase gas production and reduce HRT.

For example, a 100,000 gallon thermophilic digester, using the same feedstock (sugar) ratio will create results beginning with a profit of $378.00 per day. In addition, there is the advantage of the ability of increasing the digester temperature to 70° C. and pasteurizing all of the pathogens to create biosolids that can safely be spread on land for disposal and fertilizer value.

The wastewater sewage treatment facility based on a 100,000 gallon tank with 1% solids equates to 1,000 gallons of solids of which 50% is never converted to gas due to the hydraulic retention time of about 24 days. By the addition of sugar a high concentration of microorganisms is created that would convert not only the easily digestible sugar, but would also consume an additional 25% of the biodegradable solids present in the waste stream, solids that normally would never be converted to biogas. Most existing digesters today have approximately a 1 to 3 million gallon capacity. Since a wastewater treatment plant has existing digesters, only the apparatus and process and the additional piping and tanks for storage of feedstocks (i.e. sugar, starches) of the stand-alone digester would need to be added to create a very viable biogas generating facility.

Just a few of the savings include an increase in gas production, fewer biosolids, pathogen free biosolids, less cost for treatment of biosolids, smaller capacity and fewer digesters needed to accomplish the same processing and a shorter hydraulic retention time.

While in the foregoing specification this invention has been described in relation to certain preferred embodiments thereof and many details have been set forth for purposes of illustration; it will be apparent to those skilled in the art that the invention is susceptible to additional embodiments and that certain of the details described herein can be varied considerably without departing from the basic principles of the invention.

What is claimed is:

1. A process for converting biodegradable organic material into a product gas which leaves substantially no waste comprising:
   a. introducing a metered stream of slurry comprising a mixture of non-contaminated water and a non-toxic biodegradable feedstock containing at least 10 percent biodegradable solids, of which at least 95 percent of the solids will convert to gas, into a completely mixed thermophilic anaerobic digester at a thermophilic reaction temperature, said digester having an active, producing microbial anaerobic digestion population comprising hydrolysis fermentation organisms and methanogenic organisms suspended in fluids, said biodegradable feedstock being selected from the group of glucose, beet sugar, sugar beet molasses, sugar beet syrup, sugar beet juice, sugar cane molasses, cane sugar, sugar cane syrup, sugar cane juice, corn syrup, cereal grains, oat flour, rice flour, corn flour, wheat flour, potato juice, potato pulp, sorghum and combinations thereof;
   b. generating biogas by anaerobically digesting said mixture in said thermophilic anaerobic digester at a thermophilic reaction temperature;
   c. withdrawing said biogas from a headspace of said thermophilic digester;
   d. transferring a portion of said mixture from said thermophilic digester into a completely mixed methanogenic digester at a mesophilic reaction temperature, said digester having an active, producing microbial anaerobic digestion population comprising hydrolysis fermentation organisms and methanogenic organisms suspended in fluids;
   e. generating biogas by anaerobically digesting said mixture in said methanogenic anaerobic digester at a mesophilic reaction temperature;
   f. withdrawing said biogas from a headspace of said methanogenic digester; and
   g. using said biogas.

2. The method of claim 1 wherein the thermophilic reaction temperature is in a range of between about 46° C. and about 76° C.

3. The method of claim 2 wherein the thermophilic reaction temperature is about 56° C.

4. The method of claim 3 wherein the mesophilic reaction temperature is in a range of between about 25° C. and about 45° C.

5. The method of claim 4 wherein the mesophilic reaction temperature is about 35° C.

6. The method of claim 1 including the additional step of operating an exterior pump provided on each digester to draw fluid from the bottom of each digester and pump it to a funnel shaped outlet and plate at the top center of each digester in order to spread the liquid evenly across the top of each digester and reduce scum buildup on the top of the fluid in each digester.

7. The method of claim 6 wherein a valve is provided for introducing additional non-toxic biodegradable feedstock into the mixing line and including the additional step of mixing said additional feedstock with the fluids at the upper portions of each of said digesters.

8. The method of claim 7 wherein the hydraulic retention time in the thermophilic digester is between about 1 and about 8 days and the hydraulic retention time in the methanogenic digester is between about 4 and about 15 days.

9. The method of claim 6 including the additional step of transferring said non-toxic biodegradable feedstock from a drop tank into a plurality of holding storage tanks using a heated transfer pipeline, said pipeline having a plurality of valves and a viscosity pump therein.

10. The method of claim 9 including the additional step of metering said non-toxic biodegradable feedstock from said holding tanks through a mixing line into said thermophilic anaerobic digester using a viscosity pump.

11. The method of claim 10 wherein said feedstock is variably metered as required in order to maximize the production of biogas at any given time.

12. The method of claim 11 wherein the majority of the biogas produced is methane, and said methane is used in a manner selected from the following group: in a boiler for generating steam, in an internal combustion engine, in an energy-producing turbine, in at least one gas storage tank for later use, and in a gas burner.

13. The method of claim 11 wherein the biogas produced is used to generate steam.

14. The method of claim 11 wherein the biogas produced is used in heating the thermophilic digester.

15. The method of claim 11 wherein the biogas produced is used to operate a gas fired generator.

16. The method of claim 13 wherein the feedstock is molasses and a plurality of steam heat exchangers are used to preheat the molasses.

17. The method of claim 13 including the additional step of using the steam to generate electricity with a steam turbine.

18. The method of claim 10 wherein the quantity of feedstock introduced into said digesters is variably adjusted in anticipation of the requirements for production of gas to be supplied to an electricity generating facility.

19. The method of claim 1 wherein said feedstock contains at least 50 percent biodegradable solids, of which at least 95 percent of said solids will convert into gas.

20. The method of claim 1 wherein said feedstock contains at least 75 percent biodegradable solids, of which at least 95 percent of said solids will convert into gas.

21. The method of claim 1 wherein said feedstock contains at least 90 percent biodegradable solids, of which at least 95 percent of said solids will convert into gas.

22. The method of claim 1 wherein said feedstock is substantially fully biodegradable.

23. The method of claim I wherein a waste stream from a waste water treatment facility is mixed with said slurry, and including the additional step of retaining said mixture for at least 30 minutes at a temperature of at least 70° C. in the thermophilic digester in order to pasteurize said mixture.

24. An apparatus for converting biodegradable organic material into a product as comprising:
   a. a heated drop tank for receiving said biodegradable material;
   b. a heated line in communication with said drop tank having a pump therein for transferring said material to at least one holding tank;
   c. a thermophilic anaerobic digester containing a population of hydrolyzing anaerobic fermentation organisms at a thermophilic temperature in communication with said at least one holding tank;
   d. a methanogenic anaerobic digester containing a second population of hydrolyzing anaerobic fermentations organisms at a mesophilic temperature in communication in series with said thermophilic anaerobic digester;
   e. a plurality of pipelines and pumps for introducing and re-circulating feedstock into and between said digesters;
   f. a conical opening and splash plate inside each digester in the upper portion thereof for reducing scum and spreading re-circulated fluid inside such digester; and
   g. removal pipelines connected to the tops of each of said digesters for removing biogas from said digesters.

25. The apparatus of claim 24 wherein a gas scrubber is provided in communication with said removal pipelines, a gas compressor is provided in communication with said scrubber, and at least one gas storage tank is provided in communication with said compressor.

26. The apparatus of claim 24 wherein a steam generating boiler is provided in communication with said removal pipelines.

27. The apparatus of claim 24 wherein the biodegradable material is a mixture of water and a feedstock is selected from the group of glucose, beet sugar, sugar beet molasses, sugar beet syrup, sugar beet juice, sugar cane molasses, cane sugar, sugar cane syrup, sugar cane juice, corn syrup, cereal grains, oat flour, rice flour, corn flour, wheat flour, potato juice, potato pulp, sorghum and combinations thereof.

28. The apparatus of claim 27 wherein said feedstock is delivered to said drop tank, pumped to said at least one storage tank using a viscosity pump, and thereafter, variably metered into the thermophilic digester in controlled amounts.

29. The apparatus of claim 28 wherein said feedstock is variably metered into the methanogenic digester in controlled amounts.

30. The apparatus of claim 29 wherein said feedstock is variably metered as required to maximize production of biogas in a prescribed time for peak electricity generation demand.

31. The apparatus of claim 30 wherein a steam heat exchanger is used to heat the thermophilic digester and to pre-heat the feedstock for ease of pumping.

32. The apparatus of claim 31 wherein a steam heat exchanger is used to preheat the feedstock.

33. The apparatus of claim 24 wherein the digesters are incorporated into an existing wastewater treatment facility and improves the conversion of wastewater biodegradable solids into biogas.

34. An apparatus for converting biodegradable feedstock into a product gas comprising:
   a. a drop tank for receiving a non-toxic biodegradable carbohydrate material;
   b. a storage tank in communication with said drop tank;
   c. a viscosity pump for transferring said material from said drop tank to said storage tank;
   d. a mixing tank for adding water to said material to form a slurry;
   e. an adjustable valve for variably controlling the amount of slurry fed out of said mixing tank;
   f. a thermophilic anaerobic digester containing a population of hydrolyzing anaerobic fermentation organisms having an input in communication with said mixing tank, said digester having a first output for gas and a second output for non-gas material; and
   g. a methanogenic anaerobic digester containing a second population of hydrolyzing anaerobic fermentation organisms having a first input in communication with said mixing tank, a second input in communication with said non-gas output from said thermophilic digester, a first output for gas and a second output for non-gas material.

\* \* \* \* \*